United States Patent [19]

Stoughton et al.

[11] 4,039,664

[45] Aug. 2, 1977

[54] TOPICAL GRISEOFULVIN COMPOSITION AND METHOD

[75] Inventors: Richard B. Stoughton, Rancho Santa Fe; Richard L. Harris, Dana Point; Frank J. Dea, Newport Beach, all of Calif.

[73] Assignee: Nelson Research & Development Company, Irvine, Calif.

[21] Appl. No.: 567,392

[22] Filed: Apr. 11, 1975

[51] Int. Cl.$^2$ .................... A01N 9/28; A61K 31/71
[52] U.S. Cl. ................ 424/180; 424/DIG. 5; 424/47; 424/168; 424/361; 424/365
[58] Field of Search ............................ 424/180, 274

[56] References Cited

U.S. PATENT DOCUMENTS

| 3,634,586 | 1/1972 | Kaser et al. | 424/365 |
|---|---|---|---|
| 3,636,194 | 1/1972 | Parizeau | 424/365 X |
| 3,932,653 | 1/1976 | Stoughton | 424/285 |

FOREIGN PATENT DOCUMENTS

| 871,678 | 5/1971 | Canada | 424/365 |
|---|---|---|---|
| 794,482 | 5/1958 | United Kingdom | 424/78 |
| 2,001,768 | 10/1969 | France | 424/285 |

OTHER PUBLICATIONS

Beutel, et al., Chem. Abs., 1970, vol. 73, p. 59320q.
Laden, Chem. Abs., 1970, vol. 73, p. 102083d.

*Primary Examiner*—Dale R. Ore
*Attorney, Agent, or Firm*—Martin A. Voet

[57] ABSTRACT

There is disclosed a composition and method for topically administering griseofulvin to a human or animal in a manner such that a high degree of epidermal, especially stratum corneum, retention of griseofulvin is attained, by contacting the skin of a human or animal with an effective amount of a therapeutic composition containing griseofulvin in a vehicle system comprising 2-pyrrolidone and N-methyl-2-pyrrolidone in a ratio ranging between about 1:4 and about 4:1, said composition containing at least about 10% by weight of said vehicle system.

13 Claims, 1 Drawing Figure

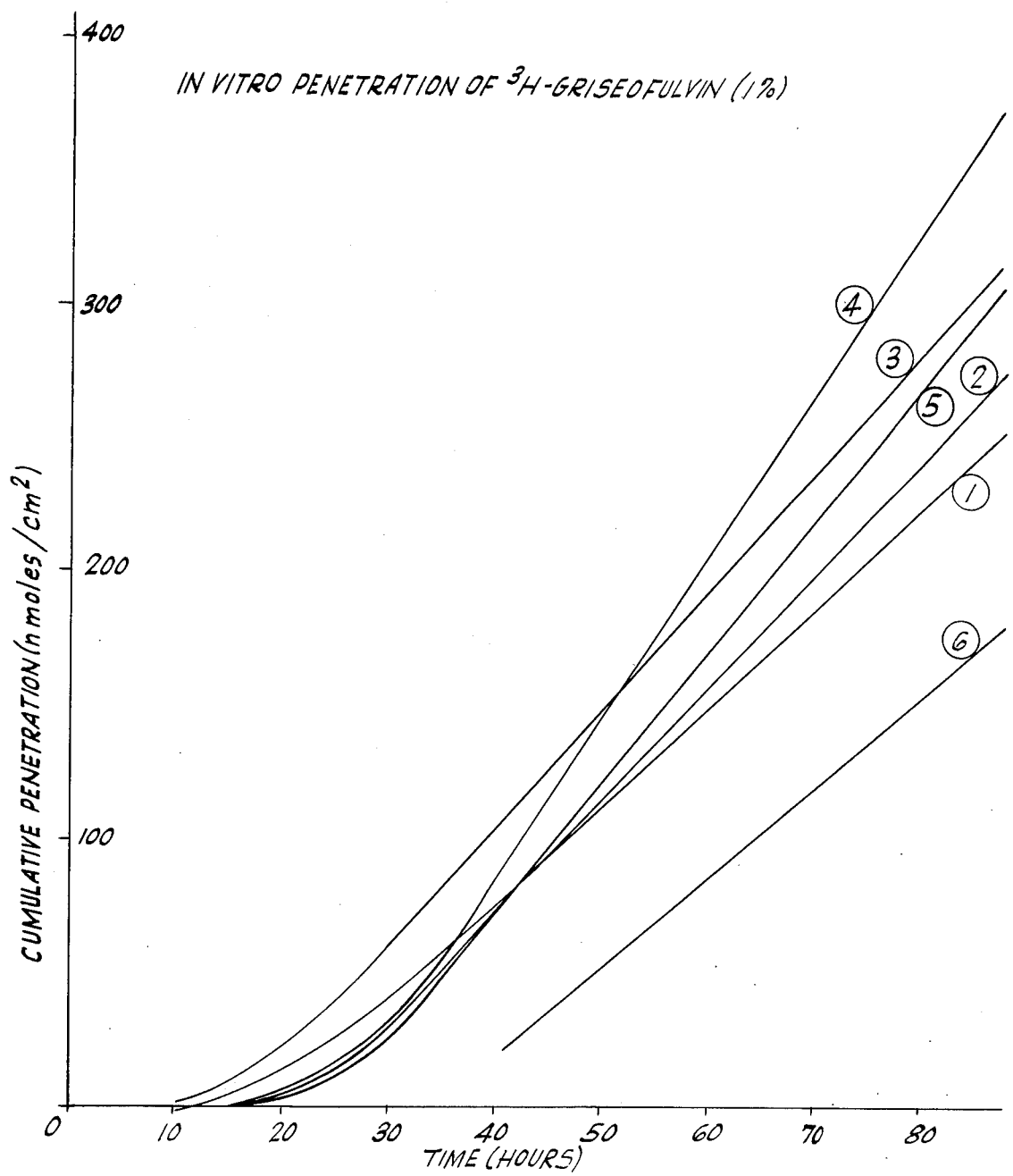

TOPICAL GRISEOFULVIN COMPOSITION AND METHOD

BACKGROUND OF THE INVENTION

1. Field of the Invention

The invention relates generally to compositions and a method for topically administering griseofulvin to humans and animals. More particularly, the present invention relates to compositions and a method whereby griseolfulvin is effectively administered topically to humans and animals and is retained by the epidermis and especially the stratum corneum in therapeutically effective amounts.

2. Background of the Prior Art

Griseofluvin is known as the treatment of choice for fungus infections of the skin and nails. Heretofore, the manner of delivery of griseolfulvin has been oral. However, it has long been known that oral treatment is not preferred because of side effects resulting from saturation of the entire body with griseofulvin and the fact that only the outer layers of affected skin need to be treated. Therefore, because fungal infections are generally infections of the skin and nails, it would be advantageous to utilize griseofulvin topically. However, despite a long-felt need for a topical griseofluvin, griseofulvin has been used orally to treat topical fungus conditions because there was not heretofore known any formulation which could be safely delivered topically which would cause sufficient retention of griseofulvin in the skin to be useful therapeutically.

Vehicles such as USP cold cream, ethanol, and various ointments, oils, solvents, and emulsions have been used to apply various chemically active ingredients locally. However, none of these are useful to cause continuous presence of therapeutically effective amounts of griseofulvin to be retained in the epidermis and especially the stratum corneum layers of the skin.

SUMMARY OF THE INVENTION

It has now unexpectedly been discovered that griseofulvin may be effectively administered topically through the use of compositions herein described.

The invention described herein generally relates to a method for topically administering griseofulvin to humans or animals and for retaining a therapeutically effective amount of griseofulvin in the epidermis whereby rapid onset and sustained duration of anti-fungal effect is obtained. The invention also relates to compositions for use in the method.

The method specifically involves contacting human or animal skin or nails with an effective amount of a composition comprising griseolfulvin in a vehicle system comprising a mixture of 2-pyrrolidone and N-methyl-2-pyrrolidone in a ratio ranging between about 1:4 and about 4:1, said composition containing at least about 10% of the vehicle system.

It has been found that through the use of the composition herein described, greater therapeutically effective amounts of griseofulvin penetrate into and are retained in the skin and/or nails and the anti-fungal effect of griseolfulvin is unexpectedly enhanced.

Both 2-pyrrolidone and N-metyl-2-pyrrolidone enhance penetration of griseofulvin. We have discovered, however, that 2-pyrrolidone and N-methyl-2-pyrrolidone act in a different manner. That is, we have found that when griseofulvin in a suitable formulation containing 2-pyrrolidone alone is contacted with human or animal skin, the anti-fungal effect is slow in onset of activity but is long in duration.

On the other hand, we have also found that when griseofulvin in a suitable formulation containing N-methyl-2-pyrrolidone is contacted with human or animal skin, the anti-fungal effect is rapid in onset of activity but short in duration.

It would be desirable to have a vehicle syste which combined the best properties of each of the foregoing compounds, that is, a vehicle system which provided for improved penetration of human or animal skin and had a reasonably rapid onset of anti-fungal activity as well as a sustained duration of anti-fungal activity.

The present invention provides such a vehicle system, as demonstrated in the Examples below. We have found that not only can this preferred vehicle system be obtained by combining 2-pyrrolidone and N-methyl-2-pyrrolidone in suitable ratios, but that the combinations have better anti-fungal activity than would otherwise be expected. That is, combinations of griseofulvin and 2-pyrrolidone and N-methyl-2-pyrrolidone are synergistic in that they produce a greater penetration of griseofulvin than can be explained by the expected additive effect of 2-pyrrolidone and N-methyl-2-pyrrolidone.

DETAILED DESCRIPTION OF THE INVENTION

The amount of griseofulvin to be used in the present invention is that amount of griseofulvin which is effective therapeutically in the treatment of fungus diseases of the type in which griseofulvin is known to be useful, that is, an amount sufficient to temporarily alleviate the signs and symptoms of fungus diseases which are known to be treatable with griseofulvin. Typical therapeutic amounts are somewhat dependent on the particular fungus and its location, but these amounts generally range from about 0.1 to about 10% and preferably about 0.5 to about 5% by weight and particularly about 1% by weight.

2-Pyrrolidone and N-methyl-2-pyrrolidone are available commercially and are made by a number of methods known to those of skill in the art as exemplified by U.S. Pat. Nos. 2,555,353 and 2,267,757. The vehicle system is formed from a mixture of 2-pyrrolidone and N-methyl-2-pyrrolidone in a ratio between about 1 to 4 and about 4 to 1 parts 2-pyrrolidone to N-methyl-2-pyrrolidone. A composition containing griseofulvin should contain at least about 10% by weight of the vehicle system. Preferred compositions for topical use contain an effective amount of griseofulvin together with from about 10 to about 40% 2-pyrrolidone and from about 10 to about 40% N-methyl-2-pyrrolidone. A particularly preferred solution form comprises an effective amount of griseofulvin, about 50% of a topical pharmaceutical carrier, e.g., ethyl alcohol, isopropyl alcohol or the like, about 20% N-methyl-2-pyrrolidone and about 30% 2-pyrrolidone.

Griseofulvin may be dissolved in a vehicle system of this invention and topically applied to affected aeas of the skin in any convenient dosage form, e.g. cream, ointment, lotion, spray, gel, aerosol, solution, etc. Typical topical pharmaceutical carriers which make up the foregoing dosage forms include water, acetone, isopropyl alcohol, freons, ethyl alcohol, polyvinyl pyrrolidone, propylene glycol, fragrances, gel-producing materials, mineral oil, stearyl alcohol, stearic acid, spermaceti, sorbitan monooleate, "Polysorbates", "Tweens", sorbital methylcellulose, etc.

The amount of the composition to be administered will obviously be an effective amount for the desired result expected therefrom. This, of course, will be ascertained by the ordinary skill of the practitioner. Due to enhanced activity which is achieved, the dosage of griseofulvin may often be decreased from that generally applicable. In accordance with the usual prudent formulation practices, a dosage near the lower end of the useful range of griseofulvin may be employed initially and the dosage increased as indicated from the observed response, as in the routine procedure of the physician.

The griseofulvin so applied is carried into the stratum corneum, and is retained in the epidermis and stratum corneum in therapeutically effective amounts and thereby successfully treats fungus-caused skin problems. Griseofulvin, thus applied, is retained by the epidermis in far higher concentrations that was heretofore known and resists being removed by washing for substantial time periods whereby a more successful therapeutic method of treatment is affected.

The examples which follow illustrate the compositions of the present invention.

EXAMPLE 1

The in vitro penetration of $^3$H-Griseofulvin in solution dosage form was evaluated by means of a conventional diffusion cell apparatus. Hairless mouse skin specimens of 80 to 83-day-old male mice were utilized. One-half ml of each test solution was applied to a 2 cm$^2$ area of skin. 20 micro-liter samples were removed from the apparatus at the indicated time intervals. The samples were assayed using a liquid scintillation counter. Each formulation tested contained 1% $^3$H-griseofulvin, 10% aqueous phosphate buffer (pH 7), 39% propylene glycol and the following percnets of 2-pyrrolidone and N-methyl-2-pyrrolidone:

| Formulation Number | N-methyl-2-pyrrolidone (%) | 2-pyrrolidone (%) |
|---|---|---|
| 1 | 50 | 0 |
| 2 | 20 | 30 |
| 3 | 40 | 10 |
| 4 | 10 | 40 |
| 5 | 30 | 20 |
| 6 | 0 | 50 |

The results of the tests are shown in the FIG. The test results show that mixtures of N-methyl-2-pyrrolidone and 2-pyrrolidone cause the penetration through the mouse skin of greater amounts of labeled griseofulvin over an extended period of time than either N-methyl-2-pyrrolidone or 2-pyrrolidone by themselves.

EXAMPLE 2

The following solution formulations were prepared:

| | Solution formulations | | |
|---|---|---|---|
| | A(%) | B(%) | C(%) |
| Griseofulvin | 1 | 1 | 1 |
| 2-Pyrrolidone | 5 | 30 | 20 |
| N-methyl-2-pyrrolidone | 5 | 20 | 30 |
| Isopropyl myristate | 5 | 5 | 5 |
| Fragrance | 0.1 | 0.1 | 0.1 |
| Adjuvant solvent qs. ad | ethanol | isopropyl alcohol | acetone |

Formulation B was tested on human subjects with fungus infections on the feet or hands. The patients indicated that the formulation stopped the itching and cleared the fungus with daily application over a period of 2–4 weeks.

EXAMPLE 3

An aerosol form of formulation B of EXAMPLE 2 is prepared by preparing the following mixture:

| Formulation B | 25% |
|---|---|
| Freon[1] | 75% |

[1]Freon is 75/25 Freon 114/12

EXAMPLE 4

The following gel formulations were prepared:

| | Gel | | |
|---|---|---|---|
| | A | B | C |
| Griseofulvin | 1% | 1% | 1% |
| 2-Pyrrolidone | 10% | 20% | 32% |
| N-methyl-2-pyrrolidone | 15% | 30% | 48% |
| Viscosity agent (Carbopol 940) | 0.75% | 0.75% | — |
| Viscosity agent (Carbopol 934) | — | — | 1% |
| Ethanol | 45.5% | 20.3% | 5.8% |
| Fragrance | 0.2% | 0.2% | 0.4% |
| Gelling agent (diethylaminoethanol) | 0.8% | 1% | — |
| Gelling agent (2',2'-diethyldihexylamine) | — | — | 1% |
| Water qs. ad | 100% | 100% | 100% |

EXAMPLE 5

The following cream formulations are prepared:

| | Cream Formulations | | |
|---|---|---|---|
| | A(%) | B(%) | C(%) |
| Griseofulvin | 1.0 | 1.0 | 1.0 |
| Stearyl alcohol, U.S.P. | 12.0 | 12.0 | 12.0 |
| Ethoxylated cholestrol (Solulan C-24) | 0.4 | 0.4 | 0.3 |
| Microcrystalline Wab (FT-200) | — | — | 3.0 |
| Synthetic spermaceti | 7.5 | 7.5 | 7.5 |
| Sorbitan monooleate (Arlacel 80) | 1.0 | 1.0 | 1.5 |
| Polysorbate 80. U.S.P. (Tween 80) | 3.0 | 3.0 | 3.5 |
| 2-Pyrrolidone | 5.0 | 10.0 | 20.0 |
| N-methyl-2-pyrrolidone | 5.0 | 15.0 | 15.0 |
| Sorbitol Solution, U.S.P. | 5.5 | 5.5 | 5.5 |
| Sodium Citrate | 0.5 | 0.5 | 0.5 |
| Chemoderm #844 Fragrance | 0.2 | 0.2 | 0.2 |
| Purified water qs. ad | | | |

EXAMPLE 6

The following stick formulation was prepared:

| Griseofulvin | 1% |
|---|---|
| Sodium stearate | 7.5% |
| 2-Pyrrolidone | 12.0% |
| N-methyl-2-pyrrolidone | 18.0% |
| Propylene glycol | 36.0% |
| Fragrance | 0.2% |
| Coloring agent | 0.001% |
| Purified water qs. ad | |

We claim:

1. A composition useful in the topical treatment of fungal infections of the skin and nails comprising an effective anti-fungal amount of griseofulvin, together with a vehicle system comprising a mixture of 2-pyrrolidone and N-methyl-2-pyrrolidone in a ratio ranging between about 1:4 and about 4:1, said composition containing at least about 10% by weight of said vehicle system.

2. The composition of claim 1 containing about 10 to about 40% by weight 2-pyrrolidone and about 10 to about 40% by weight N-methyl-2-pyrrolidone.

3. The composition of claim 1 containing about 30% by weight 2-pyrrolidone and about 20% by weight N-methyl-2-pyrrolidone.

4. The composition of claim 1 containing about 50% of an additional topical pharmaceutical carrier.

5. The composition of claim 4 wherein the topical pharmaceutical carrier comprises ethyl alcohol or isopropyl alcohol.

6. The composition of claim 1 wherein effective antifungal amount of griseofulvin is about 0.1 to about 10% by weight.

7. A composition comprising about 1% griseofulvin together with about 30% by weight 2-pyrrolidone, about 20% by weight N-methyl-2-pyrrolidone and about 49% by weight of an additional topical pharmaceutical carrier.

8. A method for therapeutically treating fungal infections of the sin and nails in humans or animals comprising contacting human or animal skin or nails with an effective amount of a therapeutic composition containing about 0.1 to about 10% by weight griseofulvin in a vehicle system comprising a mixture of 2-pyrrolidone and N-methyl-2-pyrrolidone in a ratio ranging between about 1:4 and about 4:1, said composition containing at least about 10% of said vehicle system.

9. The method of claim 8 wherein the vehicle system comprises about 10 to about 40% by weight 2-pyrrolidone and about 10 to about 40% by weight N-methyl-2-pyrrolidone.

10. The method of claim 8 wherein the vehicle system comprises about 30% by weight 2-pyrrolidone and about 20% by weight N-methyl-2-pyrrolidone.

11. The method of claim 8 wherein the composition contains about 50% of an additional topical pharmaceutical carrier.

12. The method of claim 11 wherein the topical pharmaceutical carrier comprises ethyl alcohol or isopropyl alcohol.

13. A method for therapeutically treating fungal infections of the skin and nails in humans and animals comprising contacting said human or animal skin or nails with an effective amount of a composition comprising about 1% by weight griseofulvin, about 30% by weight 2-pyrrolidone, about 20% by weight N-methyl-2-pyrrolidone and about 49% by weight of an additional topical pharmaceutical carrier.

* * * * *